(12) United States Patent
Ting

(10) Patent No.: US 7,655,080 B2
(45) Date of Patent: Feb. 2, 2010

(54) AIR CLEANING AND FILTERING SYSTEM

(76) Inventor: Kei Hang Ting, Room 8, 10/F Yan Hing Centre, 9-13 Wong Chuk Yeung St. Fo Tan, Shatin N.T., Hong Kong (CN)

( * ) Notice: Subject to any disclaimer, the term of this patent is extended or adjusted under 35 U.S.C. 154(b) by 417 days.

(21) Appl. No.: 11/565,791

(22) Filed: Dec. 1, 2006

(65) Prior Publication Data

US 2007/0186777 A1    Aug. 16, 2007

(30) Foreign Application Priority Data

Dec. 5, 2005    (CN) .................... 2005 2 0120078 U

(51) Int. Cl.
*B01D 46/00*    (2006.01)
(52) U.S. Cl. .............. 96/225; 96/223; 55/490; 55/490.1; 219/628; 422/4; 422/120; 422/123; 422/124; 422/125
(58) Field of Classification Search ............ 422/4, 422/120, 123–125; 219/628; 55/490, 490.1; 96/223, 225
See application file for complete search history.

(56) References Cited

U.S. PATENT DOCUMENTS

| | | | | |
|---|---|---|---|---|
| 2,472,011 A | * | 5/1949 | Graham | 422/124 |
| 2,557,451 A | * | 6/1951 | Merrick | 422/4 |
| 3,721,067 A | * | 3/1973 | Agnew | 95/273 |
| 3,966,407 A | * | 6/1976 | Zuckerberg et al. | 422/4 |
| 4,411,675 A | * | 10/1983 | de Castella | 96/140 |
| 4,422,369 A | * | 12/1983 | Smets | 454/191 |
| 4,435,194 A | * | 3/1984 | Picard et al. | 95/19 |
| 4,690,699 A | * | 9/1987 | Sugisawa et al. | 96/225 |
| 4,707,167 A | * | 11/1987 | Saito et al. | 96/225 |
| 4,909,999 A | * | 3/1990 | Cummings et al. | 422/298 |
| 5,632,954 A | * | 5/1997 | Coellner et al. | 422/4 |
| 5,756,047 A | * | 5/1998 | West et al. | 422/37 |
| 5,938,823 A | * | 8/1999 | Condit et al. | 96/16 |
| 7,175,699 B2 | * | 2/2007 | Aubert | 96/224 |
| 2002/0160440 A1 | * | 10/2002 | McDonnell et al. | 435/31 |
| 2003/0072688 A1 | * | 4/2003 | Matias | 422/120 |
| 2003/0177907 A1 | * | 9/2003 | Aubert | 95/283 |
| 2005/0092181 A1 | * | 5/2005 | Shih et al. | 95/283 |

* cited by examiner

*Primary Examiner*—Robert J Hill, Jr.
*Assistant Examiner*—Christopher P Jones
(74) *Attorney, Agent, or Firm*—Global IP Services; Tianhua Gu

(57) ABSTRACT

The present invention relates to an air cleaning and filtering system, comprising an air intake filtering part and an air outlet filtering part, wherein the air intake filtering part further comprises filtering devices which connect with the air inlet and the air outlet of the air intake filtering part, wherein the air intake filtering part and the air outlet filtering part further comprise sterilizing units. The air cleaning and filtering system of the present invention can provide filtering and sterilization to the incoming and outgoing air of a room to purify and circulate the indoor air and prevent the backflow of the infected air, thus preventing disease spreading through air flow. The air cleaning and filtering system of the present invention can be widely used in hospital, mobile treatment room, clinic, hotel, theatre, office, toilet, public vehicles and home, etc.

5 Claims, 5 Drawing Sheets

AIR CLEANING AND FILTERING SYSTEM

CROSS REFERENCE TO RELATED APPLICATION

This application claims the benefit of a Chinese patent application No. 200520120078.3, filed on Dec. 5, 2005.

FIELD OF THE INVENTION

The present invention relates to an air cleaning and filtering system.

BACKGROUND OF THE INVENTION

At present, due to industrial development and human activities, the atmosphere is severely polluted, thus threatening health of human beings. Furthermore, many serious epidemic diseases such as SARS and bird flu in recent years spread through air. The infected outdoor air can spread indoors along with airflow. In the hospital, air of the wards for patients of epidemic diseases is directly discharged outdoors and the viruses carried by the air threaten the safety of other people. Common air cleaning systems on the market can only clean suspending dust or particles in the air, but cannot clean the potential viruses in the air. Moreover, most air cleaning systems only clean or filter the indoor air, do not circulate the air and do not clean the air to be discharged; therefore they cannot prevent disease spreading.

SUMMARY OF THE INVENTION

This invention provides an air cleaning and filtering system aiming at the problem that most existing cleaning systems cannot disinfect viruses, clean and sterilize the air to be discharged outdoors and circulate the indoor air.

To resolve the technical problem mentioned above, the present invention provides an air cleaning and filtering system, comprising an air intake filtering part and an air outlet filtering part, the air intake filtering part further comprises filtering device which connects with the air inlet and the air outlet of the air intake filtering part, wherein the air intake filtering part and the air outlet filtering part further comprise sterilizing units.

In the air cleaning and filtering system of the present invention, further comprises a waste air backflow prevention device.

In the air cleaning and filtering system of the present invention, the sterilizing unit of the air intake filtering part comprises a disinfectant container at the bottom of a filter box and a heating device, and the filtering device is installed in the filter box.

In the air cleaning and filtering system of the present invention, the sterilizing unit of the air outlet filtering part is a filter box with two ends connecting with the inlet and the outlet of the air outlet filtering part respectively.

In the air cleaning and filtering system of the present invention, the sterilizing unit of the air outlet filtering part comprises an air conduit, a heating device and a sterilization filter installed on the air conduit, and the air conduit connects with the inlet and the outlet of the air outlet filtering part at both ends respectively.

In the air cleaning and filtering system of the present invention, the heating device is a thermal blower or a resistance wire.

In the air cleaning and filtering system of the present invention, an exhaust fan is installed at the outlet of the air intake filtering part.

In the air cleaning and filtering system of the present invention, an air intake fan is installed at the inlet of the air outlet filtering part.

The air cleaning and filtering system of the present invention can be used to filter and sterilize the incoming and outgoing air of a room to prevent disease spreading through air circulation and thus can be applied in hospital, mobile treatment room, clinic, hotel, theatre, office, toilet, public vehicles and home, etc.

BRIEF DESCRIPTION OF THE DRAWINGS

The present invention will be further described with reference to the accompanying drawings and embodiments hereinafter, in the accompanying drawings.

DETAILED DESCRIPTION OF THE PREFERRED EMBODIMENT

Figure 1:
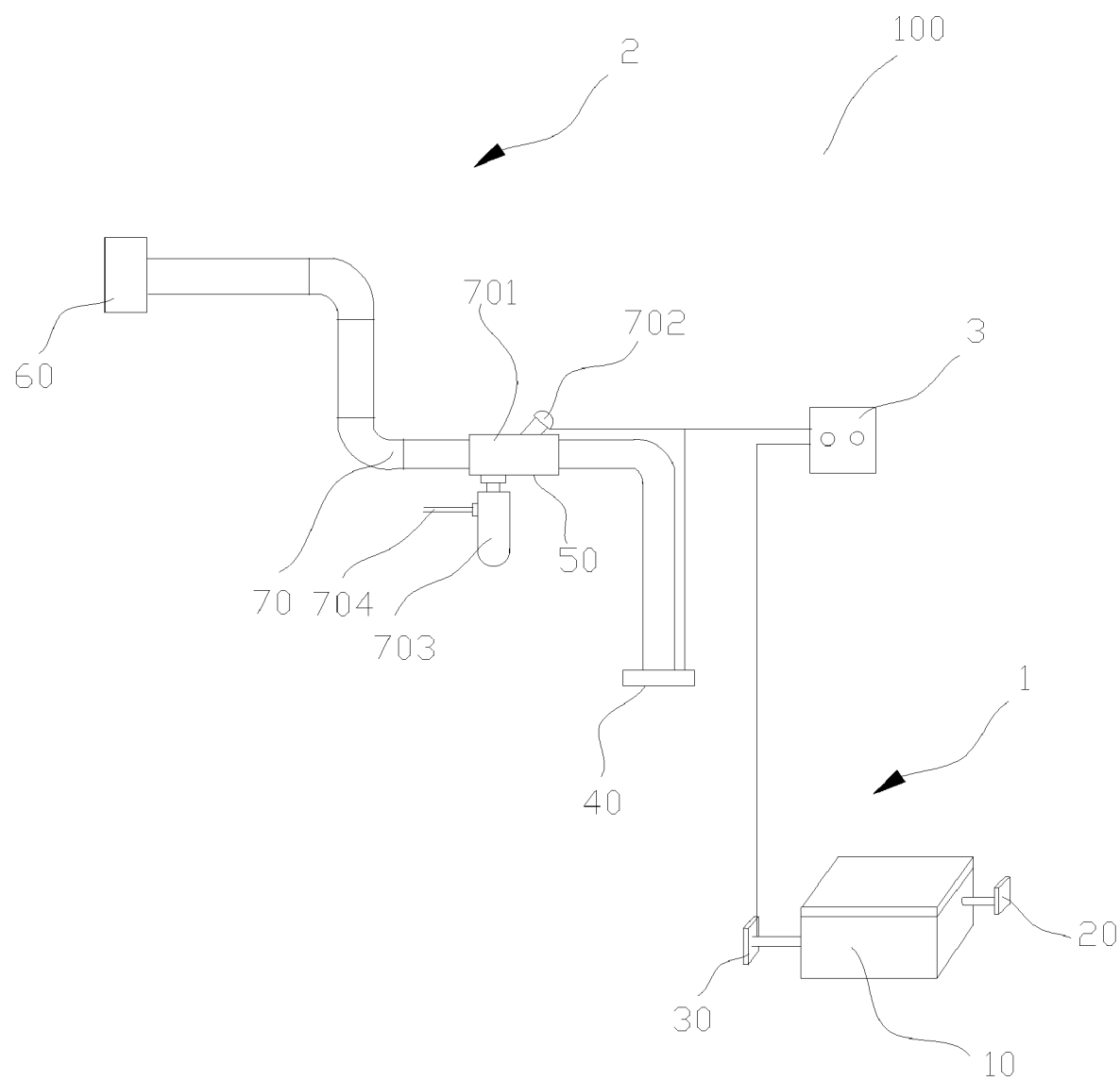
FIG. 1 is a schematic view of a first embodiment of the air cleaning and filtering system according to the present invention.
Figure 2:
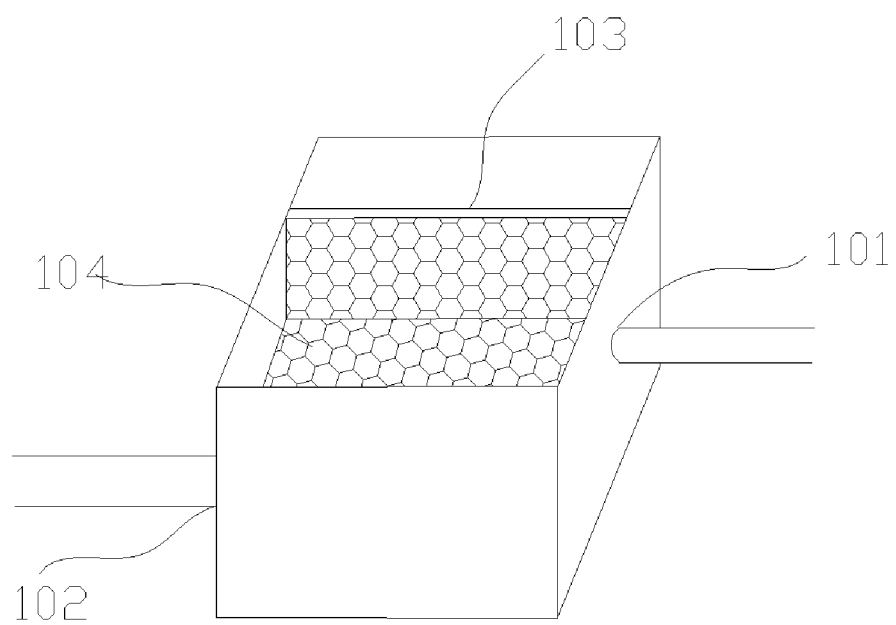
FIG. 2 is a partial schematic view of the filter box.

In the embodiment of the present invention as shown in FIGS. 1 and 2, the air cleaning and filtering system 100 comprises an air intake part 1 and an air outlet part 2, both of which connect with the power switch 3. The air intake part 1 comprises a filter box 10, an air inlet 20 connecting with the air intake end 101 of the filter box 10, and an exhaust fan 30 connecting with the air outlet end 102 of the filter box 10. Advantageously, an air intake fan is installed at the air inlet 20 to supply more fresh air.

Figure 3:
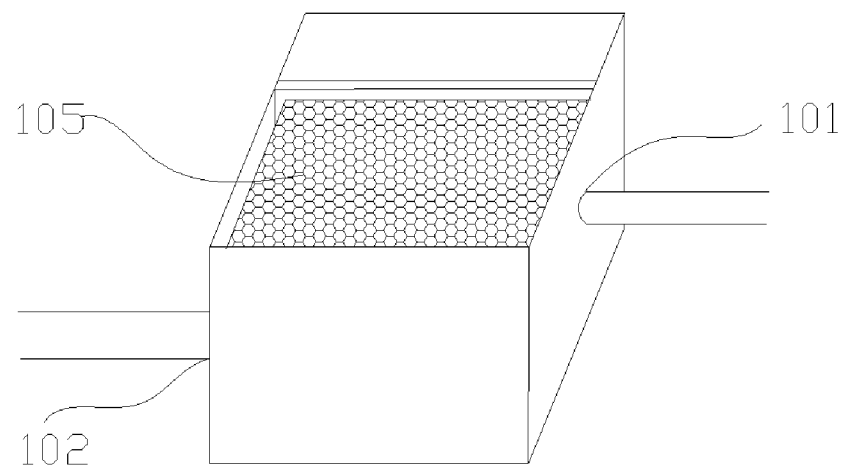
FIG. 3 is another partial schematic view of the filter box.
Figure 4:
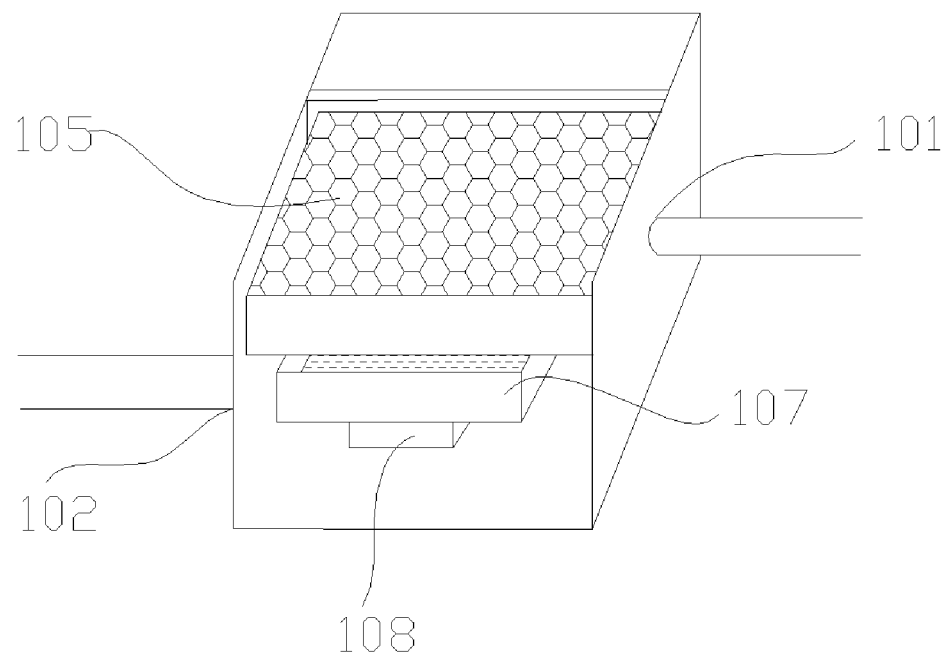
FIG. 4 is cutaway view of the filter box in FIG. 3.

As shown in FIGS. 2, 3 and 4, perforated clapboard 103 and 104 are set in the filter box 10, wherein filtering material 105 such as sponge or active carbon is laid on the clapboard 104. Below the clapboard 104, a disinfectant container 107. and a heating device 108 are equipped. The heating device 108 can be resistance wires and is used to heat the disinfectant in the container to vaporize it and mix with air. When outdoor air enters into the filter box 10, the filter material 105 filters it and clears away fine dust and particles carried along, then the disinfectant sterilizes the air.

Figure 5:
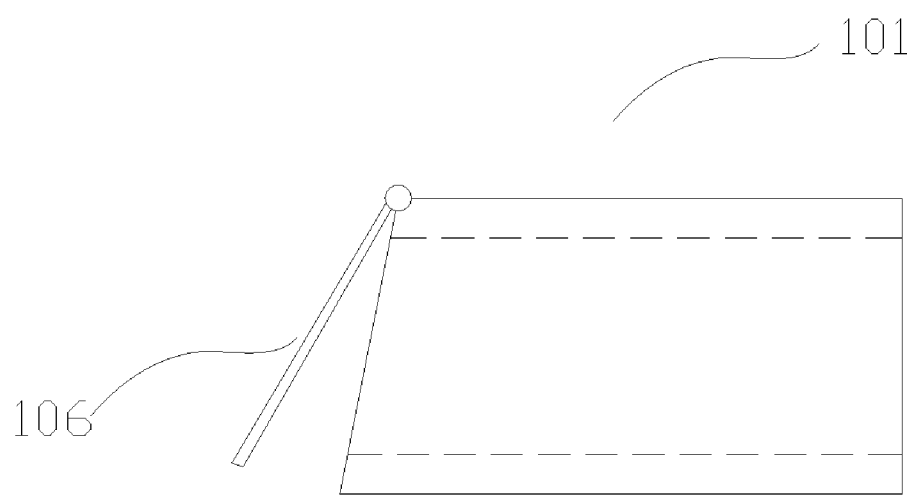
FIG. 5 is a partial schematic view of the inlet of the filter box.

As shown in FIG. 5, at the air intake end 101 of the filter box 10, a waste air backflow prevention device is installed, which is a metal sheet 106 hinged on one end of the air intake conduit, wherein the metal sheet 106 is slightly larger than the air intake conduit and can rotate around the hinge point. When air enters, the metal sheet 106 is blown upward to allow the outdoor air to come in, while when the air backflows, the metal sheet 106 clings to the air intake conduit tightly to prevent backflow.

As shown in FIG. 1, the air outlet filtering part 2 comprises an air intake fan 40, a sterilizing chamber 50 and an air outlet 60. Advantageously, an exhaust fan is installed at the air outlet 60. The air intake fan 40 and the air outlet 60 connect with the sterilizing chamber 50 through a conduct 70 respectively. At the elbows of the conduct 70, metal hoses are used and other parts can be made from PVC plastic.

The sterilizing chamber 50 comprises an air conduit 701 with two ends connecting with the conduct 70, and a heating device 702 installed at one side of the conduct. In the embodiment of the present invention, the heating device 702 is a thermal blower to heat the air passing through the conduit 701 to achieve sterilization. Other heating methods can also be used, such as installing a resistance wire in the air conduit 701 or directly equipping a heating sleeve around the conduit 701. The air conduit 701 is made of metal for better heat dispersion. At the other side of the conduit 701, a disinfecting filter 703 is installed, on which a hose 704 is set to convey the disinfectant to the disinfecting filter 703. The indoor air enters through the air intake fan 40, is heated and sterilized by the disinfectant in the sterilizing chamber 50 and then discharged through the air outlet 60.

Figure 6:
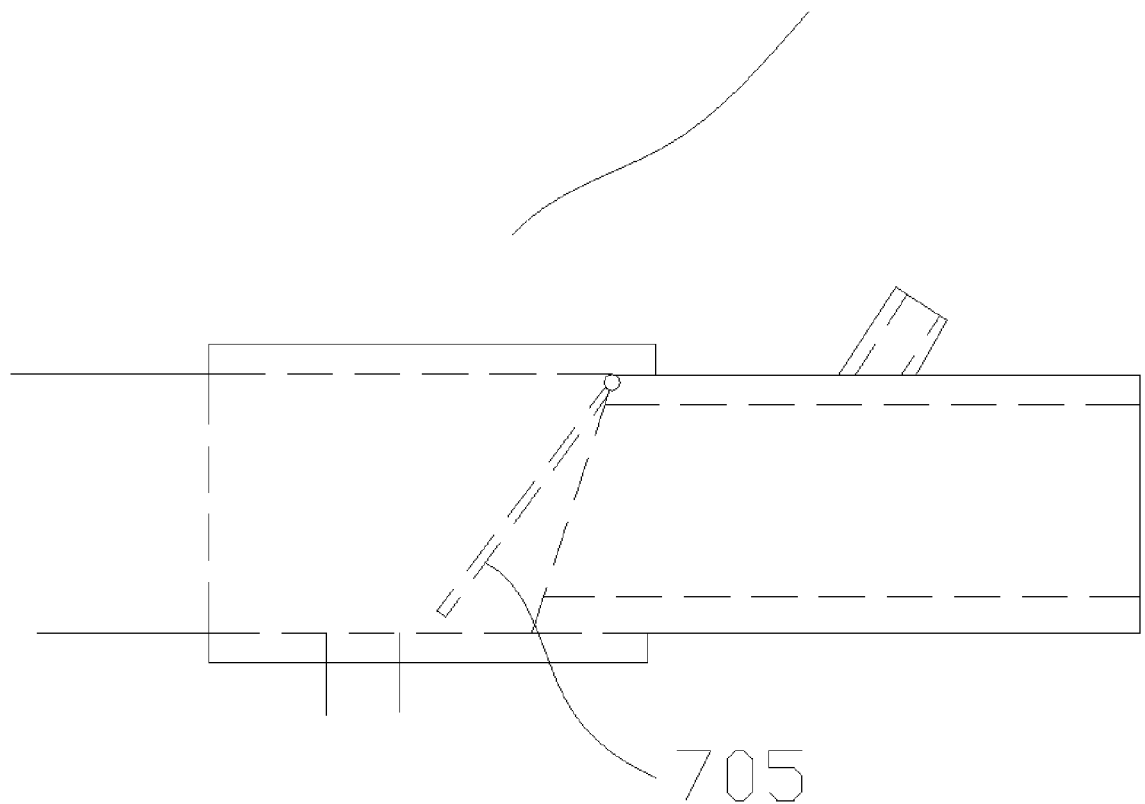
FIG. 6 is a schematic view of the air conduit.

As shown in FIG. 6, the air conduit consists of two parts of different diameters. At the thinner end, a waste air backflow prevention device is also installed, which is a metal sheet 705 and the same as the metal sheet 106 in terms of structure. In the present invention, the waste air backflow prevention device can also be other device as one-way valve, etc.

Figure 7:
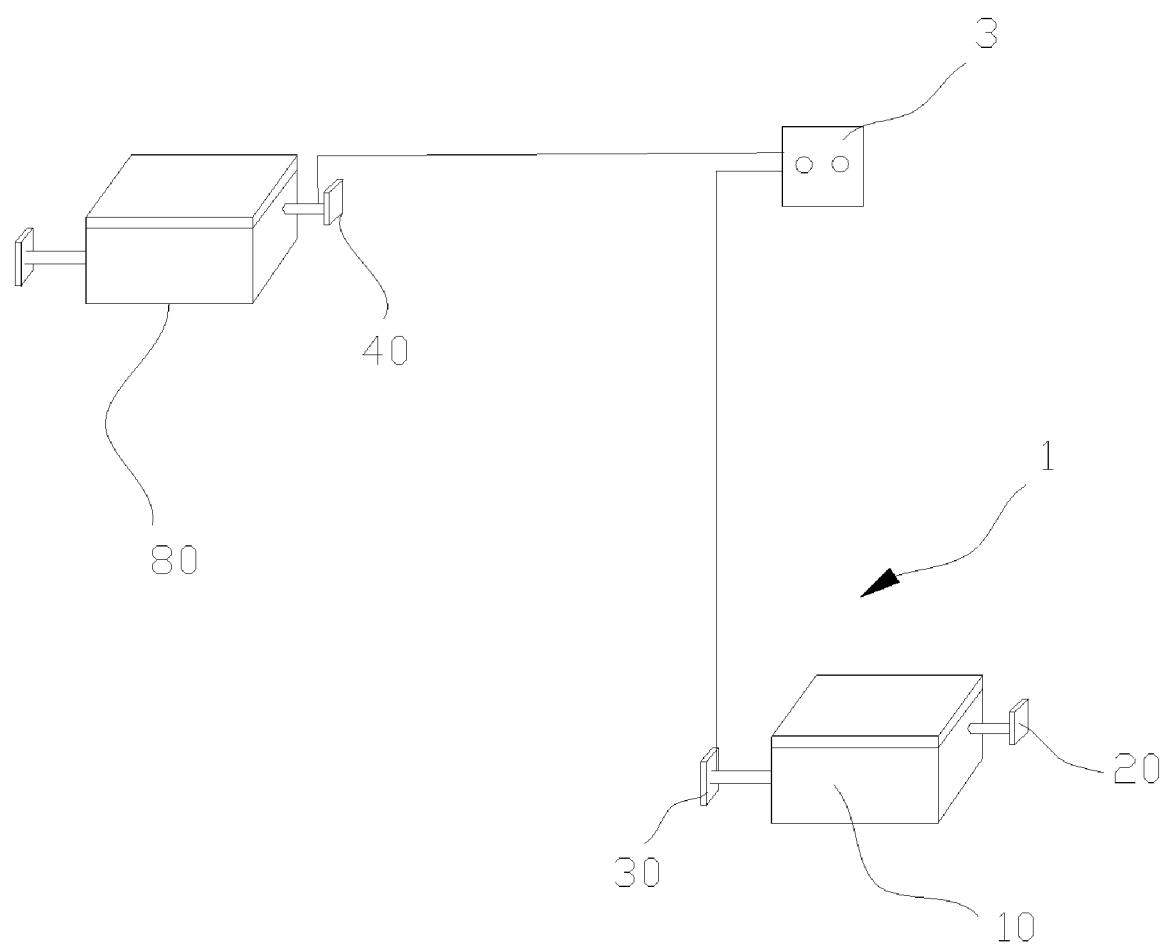
FIG. 7 is a schematic view of a second embodiment of the air cleaning and filtering system according to the present invention.

In the second embodiment of the present invention as shown in FIG. 7, the filter box 80 can also be installed in the air outlet filtering part 2. It is the same with that in the air intake filtering part 1 and functions the same. This structure can achieve the same disinfecting action, and is convenient for carrying.

In actual applications, different disinfectants can be used for different viruses, so as to sterilizing plurality kinds of viruses.

In actual applications, the air intake filtering part 1 is installed in the lower wall corner and the air outlet filtering part 2 is mounted on the ceiling or on the wall to circulate, heat and disinfect the indoor air to prevent spreading of diseases. The present invention can be used in hospital, home and public places, etc.

What is claimed is:

1. An air cleaning and filtering system comprising: an air intake filtering part; an air outlet filtering part, which is separated from the air intake filtering part; the air intake filtering part further comprising a filtering device connected with the air inlet and the air outlet of the air intake filtering part; the air intake filtering part and the air outlet filtering part further comprising sterilizing units respectively; a waste air backflow prevention device installed at a air intake end of the filter device including a sheet hinged on one end of the air intake end and the sheet is larger than the air intake end; wherein the sterilizing unit of the air intake filtering part comprises a disinfectant container and a heating device at the bottom of a filter box; and the filtering device is installed in the filter box; wherein perforated clapboards are set in the filter box, filtering material is laid on the clapboard and the disinfectant container and the heating device are equipped below the clapboard.

2. The air cleaning and filtering system according to claim 1, wherein the sterilizing unit of the air outlet filtering part is a filter box having a disinfectant container with two ends connecting with the inlet and the outlet of the air outlet filtering part respectively.

3. The air cleaning and filtering system according to claim 1, wherein the sterilizing unit of the air outlet filtering part comprises an air conduit, a heating device made of a thermal blower and a disinfecting filter installed on the air conduit; and the air conduit connects with the inlet and the outlet of the air outlet filtering part at both ends respectively.

4. An air cleaning and filtering system as claimed in claim 1, wherein an exhaust fan is installed at the outlet of the air intake filtering part.

5. An air cleaning and filtering system as claimed in claim 1, wherein an air intake fan is installed at the inlet of the air outlet filtering part.

\* \* \* \* \*